US011129429B2

(12) United States Patent
Hinds et al.

(10) Patent No.: US 11,129,429 B2
(45) Date of Patent: *Sep. 28, 2021

(54) TEXTILE MATERIALS WITH SPONTANEOUS EMISSION AND METHODS OF UV PROTECTION, SHADING, WARMING, AND OTHER APPLICATIONS USING SAME

(71) Applicant: Lumia Group, LLC, Charlotte, NC (US)

(72) Inventors: Robert Gates Hinds, Charlotte, NC (US); Marco Scipioni, Charlotte, NC (US)

(73) Assignee: Lumia Group, LLC, Charlotte, NC (US)

( * ) Notice: Subject to any disclaimer, the term of this patent is extended or adjusted under 35 U.S.C. 154(b) by 167 days.

This patent is subject to a terminal disclaimer.

(21) Appl. No.: 16/403,936

(22) Filed: May 6, 2019

(65) Prior Publication Data

US 2020/0060368 A1   Feb. 27, 2020

Related U.S. Application Data

(63) Continuation-in-part of application No. 16/127,463, filed on Sep. 11, 2018, now Pat. No. 10,322,297.
(Continued)

(51) Int. Cl.
*A61N 5/06* (2006.01)
*A41D 31/32* (2019.01)
(Continued)

(52) U.S. Cl.
CPC ............. *A41D 31/32* (2019.02); *A41D 1/002* (2013.01); *A41D 31/065* (2019.02);
(Continued)

(58) Field of Classification Search
CPC ................ A61B 5/6803; A61B 5/6804; A61N 2005/063; A61N 2005/0645;
(Continued)

(56) References Cited

U.S. PATENT DOCUMENTS 8,084,377 B2   12/2011   Kreindel et al.
10,322,297 B1 *  6/2019   Hinds .................. A61B 5/6804
(Continued)

FOREIGN PATENT DOCUMENTS

WO   2009/154473 A2   12/2009

OTHER PUBLICATIONS

Press Release for Quantum Bio-Medicals Ltd., "Photo Therapeutic Medical Garment, Wearable full body skin solution, Regeneration Medication", HongKong, Jan. 13, 2013.
(Continued)

*Primary Examiner* — Jon Eric C Morales
(74) *Attorney, Agent, or Firm* — Morgan, Lewis & Bockius LLP

(57) ABSTRACT

Methods and associated light management system variously provide protection of at least UPF 50, a cooling effect, a shading effect, a warming effect and a source for a photovoltaic device. A textile material absorb incident spectrum including one or more of a UV wavelength, a visible wavelength, and a near infrared wavelength and spontaneously emits light having an emission spectrum including visible light radiation and near infrared radiation. The textile material and associated articles have a high degree of UV blocking property due to strong absorption in the UV range. In addition, the spontaneous emission releases most of the absorbed energy and, therefore, the textile material remains relatively cool under sunlight, the shading effect. Furthermore, the strong spontaneous emission allows for shielding properties even when the apparel is made from otherwise
(Continued)

sheer knit or weave structure. Associated application methods and manufacture methods are also disclosed.

39 Claims, 13 Drawing Sheets

Related U.S. Application Data

(60) Provisional application No. 62/720,544, filed on Aug. 21, 2018.

(51) Int. Cl.
*A41D 31/06* (2019.01)
*A41D 1/00* (2018.01)
*A61B 5/00* (2006.01)

(52) U.S. Cl.
CPC ...... *A41D 2400/10* (2013.01); *A41D 2400/26* (2013.01); *A61B 5/6804* (2013.01); *A61N 5/0616* (2013.01); *D06M 2200/25* (2013.01); *D10B 2401/13* (2013.01); *D10B 2401/18* (2013.01); *D10B 2401/22* (2013.01); *D10B 2501/04* (2013.01)

(58) Field of Classification Search
CPC .... A61N 2005/0647; A61N 2005/0651; A61N 2005/0656; A61N 2005/0659; A61N 2005/0661; A61N 2005/0662; A61N 5/0616; Y02E 10/52
See application file for complete search history.

(56) References Cited

U.S. PATENT DOCUMENTS

| | | |
|---|---|---|
| 2005/0111813 A1 | 5/2005 | Hajto et al. |
| 2006/0041039 A1 | 2/2006 | Fenyvesi et al. |
| 2008/0179573 A1 | 7/2008 | Kreindel et al. |
| 2009/0201462 A1 | 8/2009 | Gruber |
| 2011/0284729 A1 | 11/2011 | Abouraddy et al. |
| 2012/0024345 A1 | 2/2012 | Reisfeld et al. |
| 2012/0060897 A1 | 3/2012 | Bomm et al. |
| 2014/0218792 A1 | 8/2014 | Krogman et al. |
| 2015/0177423 A1 | 6/2015 | Scipioni |
| 2017/0071135 A1 | 3/2017 | Aikala |

OTHER PUBLICATIONS

Driggers (edited by), "Encyclopedia of Optical Engineering; Fourier Transform Infrared Spectroscopy", Marcel Dekker, Inc., New York Basel, 2003, pp. 607-614.

Verbunt et al., "Increased efficiency of luminescent solar concentrators after application of organic wavelength selective mirrors", Optics Express, vol. 20, No. S5, published Jul. 18, 2012, pp. A655-A668.

International Search Report and Written Opinion dated Nov. 14, 2019, issued in corresponding International Patent Application No. PCT/US19/047517.

International Preliminary Report on Patentability dated Feb. 23, 2021, issued in corresponding International Patent Application No. PCT/US19/047517.

\* cited by examiner

FIG. 8
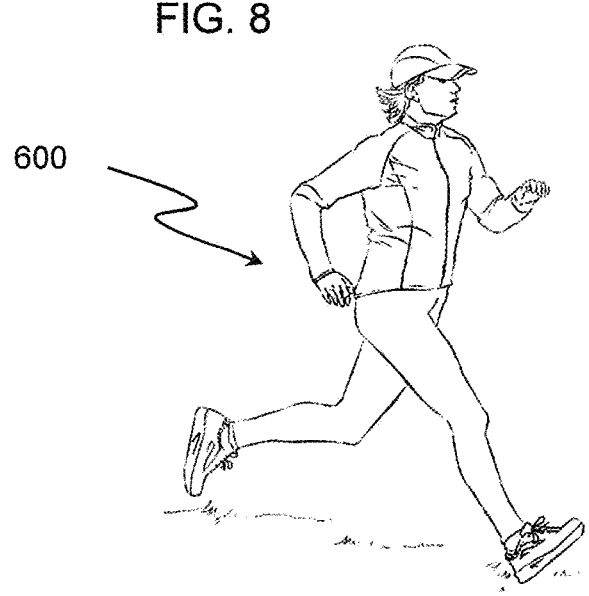
FIG. 9
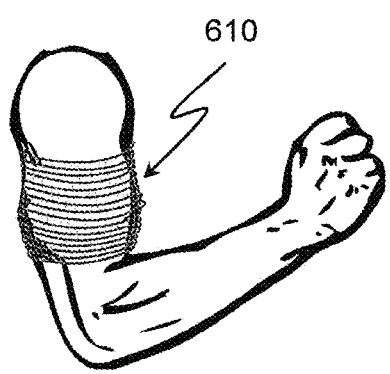
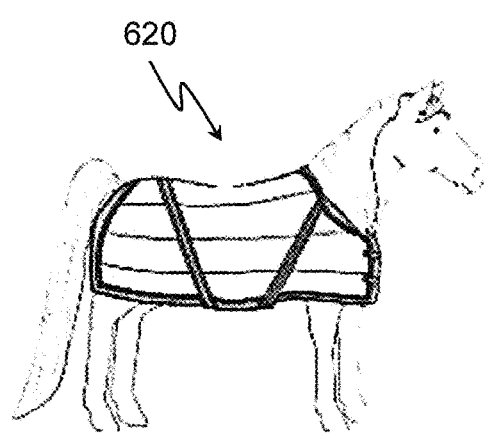
FIG. 10

TEXTILE MATERIALS WITH SPONTANEOUS EMISSION AND METHODS OF UV PROTECTION, SHADING, WARMING, AND OTHER APPLICATIONS USING SAME

RELATED APPLICATION DATA

This application is a continuation-in-part application of U.S. application Ser. No. 16/127,463, filed Sep. 11, 2018, which claims priority under 37 U.S.C. § 119 to U. S. Provisional Application No. 62/720,544, filed Aug. 21, 2018, the entire contents of each are incorporated herein by reference.

FIELD OF THE DISCLOSURE

The present disclosure relates to a light management system having an article of apparel that absorbs light spectrum from ultra-violet (UV) to near-infrared (NIR) and spontaneously emits light in the visible/near infrared spectrum. The article of apparel has a high degree of UV blocking property due to strong absorption in the UV range. In addition, the spontaneous emission is strong to the point that the article of apparel releases most of the absorbed energy and therefore remains relatively cool under sunlight, the shading effect. The strong spontaneous emission allows for shielding properties even when the apparel is made from otherwise sheer knit or weave structure. Furthermore, the strong spontaneous emission reduces the bacteria population that break down sweat therefore reducing body odor. Additionally, the strong spontaneous emission when directed toward a secondary layer provides a warming effect under sunlight in cold weather. The present disclosure also relates to an article of apparel and other textile-based structures that emits light in the visible/near infrared spectrum per se, such as clothing, footwear, head covering, athletic gear, bedding, towels, and sun shade structures.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art against the present invention.

Sunlight is a main source of energy on earth. When sunlight interacts with apparel it can result in several unwanted outcomes for the human body, like excess heat and overexposure to ultraviolet radiation. Products, such as sunscreens and other personal care products, and methods, such as shading or cooling, have been developed to mitigate these effects.

SUMMARY

Light management apparel includes clothing items that manage the interaction of sunlight with the body to reduce unwanted outcomes and/or create positive outcomes. For example, light management apparel can reduce the heat effect of sunlight on hot days, increase the heat effect of sunlight on cold days, lessen ultraviolet radiation to the body, and minimize various bacteria known to cause body odor. Such light management apparel can mitigate the effects of sunlight experienced by the human body. In other aspects, light management textiles, whether in apparel or in other structures, such as sunshade devices, can also manage this interaction. In still further aspects, the light management textile/apparel can be coupled with a photovoltaic device.

The present disclosure is directed to a light management system with an article of apparel that absorbs an incident spectrum including one or more of a UV wavelength, a visible wavelength, and a near infrared wavelength and spontaneously emits light having an emission spectrum including visible light radiation and near infrared radiation. Light is emitted from a textile material consisting of a network of yarns (as well as the article of apparel incorporating such a textile material) and the emitted light has an emission spectrum including visible light radiation and near infrared radiation.

An exemplary embodiment of a light management system comprises an article of apparel that absorbs an incident spectrum including one or more of a UV wavelength, a visible wavelength, and a near infrared wavelength and emits light having an emission spectrum including one or more of visible light radiation and near infrared radiation, where the quantum efficiency is more than 50% at near-infrared wavelengths and is more than 90% in the visible wavelengths. The energy released from the article of apparel in the form of visible light radiation and near infrared radiation reduces the stored energy in the article of apparel, hence making the article of apparel cooler under sunlight than otherwise would be (shading effect).

An exemplary embodiment of a light management system comprises an article of apparel that absorbs an incident spectrum including one or more of a UV wavelength, a visible wavelength, and a near infrared wavelength and strongly emits light having an emission spectrum including one or more of visible light radiation and near infrared radiation. The strong absorption in the UV range of the spectrum makes the article of apparel a UV blocker.

An exemplary embodiment of a light management system comprises an article of apparel that absorbs an incident spectrum including one or more of a UV wavelength, a visible wavelength, and a near infrared wavelength and strongly emits light having an emission spectrum including one or more of visible light radiation and near infrared radiation. A strong spontaneous emission in the visible wavelengths allows for shielding properties even when the apparel is made from otherwise sheer knit or weave structure.

An exemplary embodiment of a light management system comprises an article of apparel that absorbs an incident spectrum including one or more of a UV wavelength, a visible wavelength, and a near infrared wavelength and strongly emits light having an emission spectrum including one or more of visible light radiation and near infrared radiation. A strong spontaneous emission in one or more of the visible wavelengths and near infrared wavelengths causes the backside of the article of apparel to be lit.

An exemplary embodiment of a light management system comprises an article of apparel that absorbs an incident spectrum including one or more of a UV wavelength, a visible wavelength, and a near infrared wavelength and strongly emits light having an emission spectrum including one or more of visible light radiation and near infrared radiation. A strong spontaneous emission in one or more of the visible wavelengths and near infrared wavelengths is directed to the under layer, so the wearer would be warmer than otherwise would be.

An exemplary embodiment of a method of manufacture comprises mixing a first textile grade, polymeric host material and at least one of a first fluorescent component and a second fluorescent component using extrusion techniques to form a masterbatch, wherein a concentration of the fluorescent component in the masterbatch is 1% to 20%, mixing the masterbatch with a volume of a second textile grade, polymeric host material to produce a feedstock in which a total amount of fluorescent component in the feedstock is 0.01 wt. % to 1 wt. %, processing the feedstock into flat yarn, and processing the flat yarn by texturing to form a textured yarn or by cutting to form a staple yarn. The first fluorescent component has a quantum efficiency of more than 90% for emission at visible wavelengths and the second fluorescent component has a quantum efficiency of more than 50% for emission at near infrared wavelengths, and when exposed to visible light, the textured yarn or staple yarn emits radiation having an emission spectrum including at least one peak in a range of 600 nm to 1200 nm.

BRIEF DESCRIPTION OF THE DRAWINGS

The foregoing summary, as well as the following detailed description of the embodiments, can be better understood when read in conjunction with the appended drawings. It should be understood that the embodiments depicted are not limited to the precise arrangements and instrumentalities shown.

FIGS. 7 to 10 show example articles of apparel.

DETAILED DESCRIPTION

Figure 1:
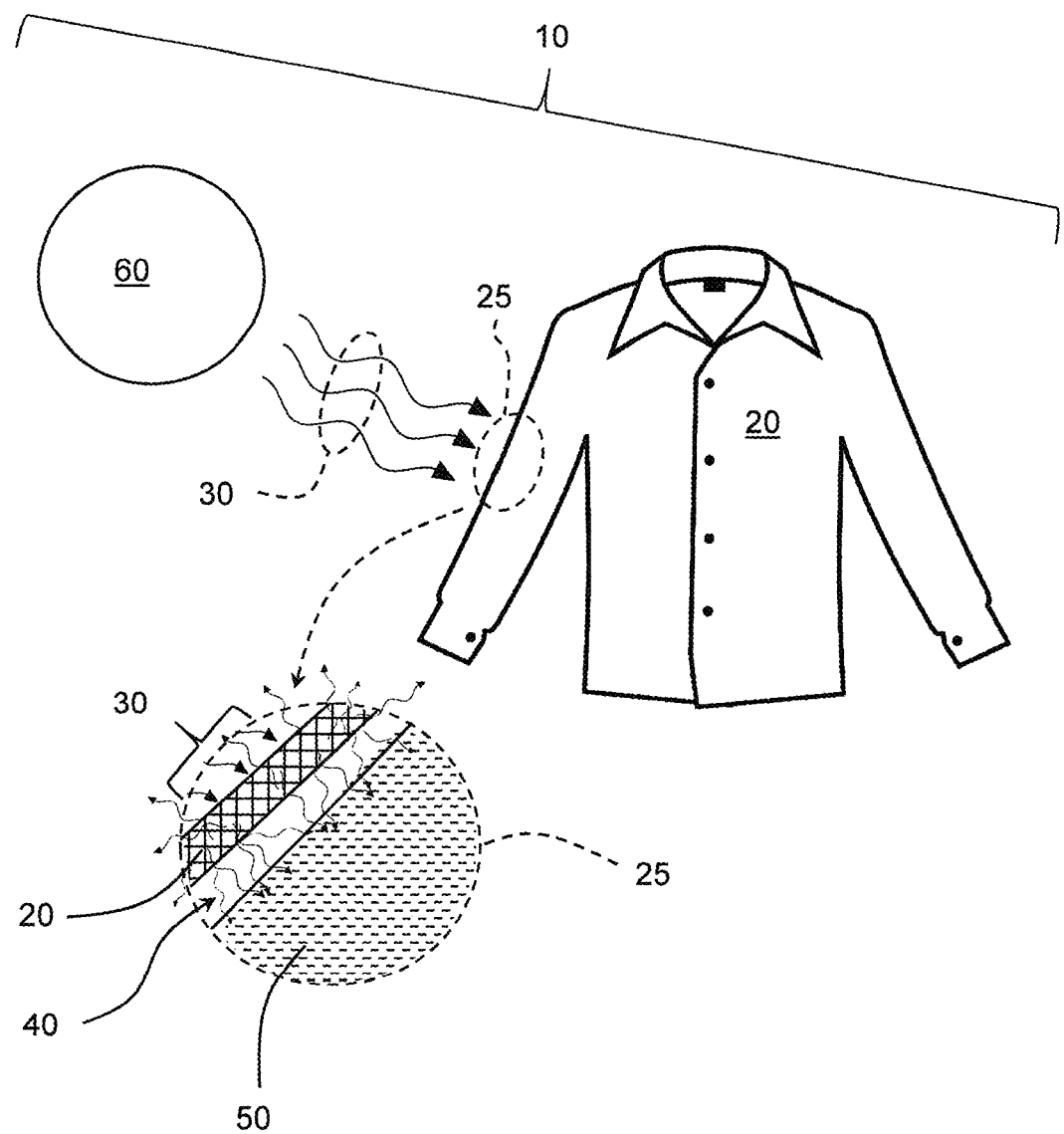
FIG. 1 schematically depicts an exemplary embodiment of a light management system.

FIG. 1 shows a light management system 10 that absorbs an incident spectrum including one or more of a UV wavelength, a visible wavelength, and a near infrared wavelength and spontaneously emits light having an emission spectrum including visible light radiation and near infrared radiation. In the example light management system 10, an article of apparel 20 absorbs an incident spectrum 30 and spontaneously emits light 40 in all directions 50 including toward a person wearing the article of apparel 20 (see magnified view 25 showing light 40 having an emission spectrum including one or more of visible light radiation and near infrared radiation is emitted from the article of apparel 20 in all directions 50 including toward person wearing the article of apparel 20).

In exemplary embodiments, the incident spectrum 30 includes one or more of a UV wavelength (meaning radiation having wavelengths of 200 to 400 nm), a visible wavelength (meaning radiation having wavelengths of 400 to 700 nm), and a near infrared wavelength (meaning radiation having wavelengths of 700 to 1200 nm). The incident spectrum 30 originates in a source 60 that is external to the article of apparel 20. In some embodiments, the source 60 is a source of natural light and can include the sun, whether or not directly incident on the article of apparel 20. In alternative embodiments, the source 60 is an artificial source of a spectrum that replicates some or all of the spectrum emitted by the sun.

In exemplary embodiments, the article of apparel 20 absorbs at least a portion of the incident spectrum 30 and emits light 40 having an emission spectrum including one or more of visible light radiation (meaning radiation having wavelengths of 400 to 700 nm) and near infrared radiation (meaning radiation having wavelengths of 700 to 1200 nm). The emission spectrum includes at least one peak in a range of 600 nm to 1200 nm. For example, in exemplary embodiments, the emission spectrum includes one or more of a first peak between 700 nm and 800 nm with a full width at half maximum (FWHM) of 80 nm to 200 nm, alternatively 100 nm to 150 nm, and a second peak between 800 nm and 900 nm with a full width at half maximum (FWHM) of 80 nm to 200 nm, alternatively 100 nm to 150 nm. In another example, in exemplary embodiments, the emission spectrum includes one or more of a first peak between 590 nm and 700 nm with a full width at half maximum (FWHM) of 50 nm to 100 nm and a second peak between 700 nm and 900 nm with a full width at half maximum (FWHM) of 50 nm to 150 nm.

Figure 2:
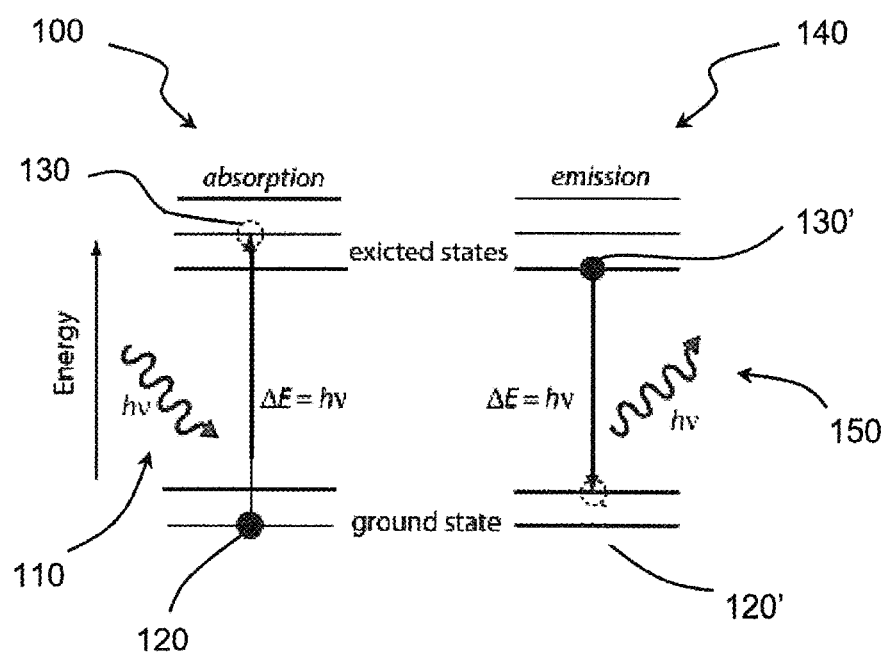
FIG. 2 schematically illustrates a process of absorption and spontaneous emission.

In this context and as schematically illustrated in FIG. 2, an exemplary process of absorption 100 of at least a portion of the incident spectrum 110 includes incident radiation 110 interacting with a portion of the article of apparel 20 resulting in an electron being raised from a ground state 120 to an excited state 130. Subsequently, emission occurs between specific energy bands, such as from a lowest excited state to an excited state closest to the ground state. Such an emission process is illustrated in FIG. 2, which schematically illustrates the process of emitting light (or emission) 150 including an electron in excited state 130' (which is in the lowest excited state) returning to a lower energy level state 120' (which is in the lowest excited state) accompanied by emitted light 150. This absorption-excitation-deexcitation-emission cycle is the basis for the disclosed light management apparel that reduces the heat effect of sunlight on hot days, increase the heat effect of sunlight on cold days, lessens ultraviolet radiation to the body, and minimizes various bacteria known to cause body odor.

Figure 3:
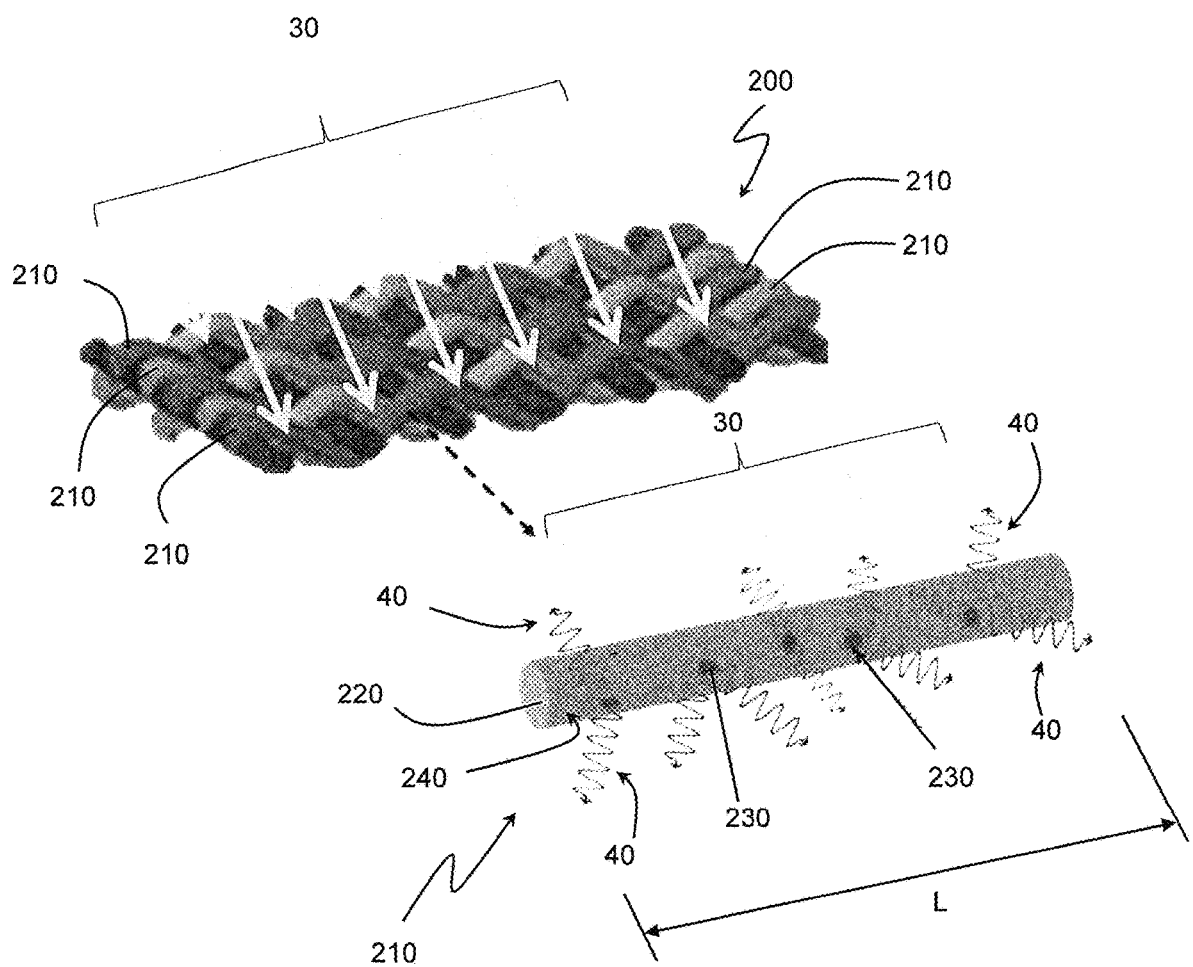
FIGS. 3A and 3B are magnified, schematic illustrations depicting a portion of an article of apparel (FIG. 3A) and an individual yarn (FIG. 3B) absorbing at least a portion of incident spectrum and emitting light having an emission spectrum.

FIG. 3A is a magnified, schematic illustration depicting a portion 200 of an article of apparel 20 absorbing at least a portion of incident spectrum 30 that includes one or more of a UV wavelength, a visible wavelength, and a near infrared wavelength and emitting light 40 having an emission spectrum including one or more of visible light radiation and near infrared radiation. As seen in FIG. 3A, the portion 200 of the article of apparel 20 includes one or more yarns 210. An individual yarn 210 is schematically depicted in FIG. 3B. Yarn 210 includes a textile grade, polymeric host material 220 and one or more fluorescent components 230. Incident spectrum 30 interacts with the yarn 210 (resulting in an electron being raised from a ground state to an excited state as previously described with reference to FIG. 2) and emitted light 40 having an emission spectrum (resulting from the electron in the excited state returning to the ground state as previously described with reference to FIG. 2) is subsequently emitted from the side surfaces 240 of the yarn 210. In being emitted from the side surfaces 240 of the yarn 210, the emission spectrum is emitted from a plurality of locations along a length (L) of the yarns 210.

Figure 4:
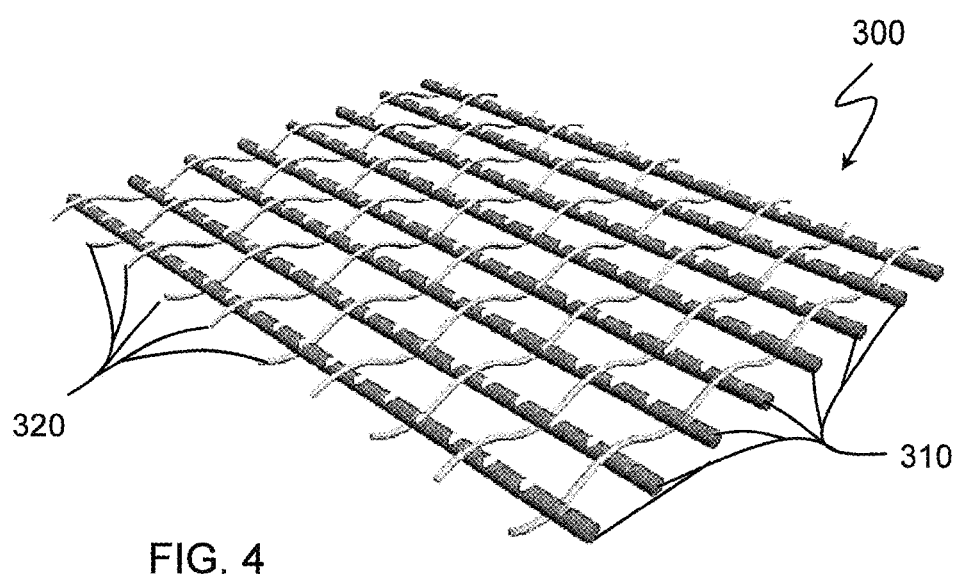
FIG. 4 is a schematic drawing of a network of yarns.

The yarns may be included in an article of apparel as a discrete yarn or a plurality of discrete yarns incorporated into a textile material, or as a plurality of similar or dissimilar yarns combined to form a network of yarns. FIG. 4 is a schematic drawing of a network of yarns 300. In exemplary embodiments, the network of yarns 300 includes a plurality of a first yarn type 310 and a plurality of a second yarn type 320. The different yarn types can be incorporated into the textile material in any suitable manner; for example, the weft yarns can be of a first yarn type and the warp yarns can be of a second yarn type. Either of the weft yarns or the warp yarns or both can be yarns that absorb an incident spectrum including one or more of a UV wavelength, a visible wavelength, and a near infrared wavelength and emits light having an emission spectrum including one or more of visible light radiation and near infrared radiation.

However, any, a subset, or all of the yarns in the network of yarns 300 can be yarns that absorb an incident spectrum including one or more of a UV wavelength, a visible wavelength, and a near infrared wavelength and emits light having an emission spectrum including one or more of visible light radiation and near infrared radiation. Accordingly, the network of yarns can incorporate one or more yarn types that absorb an incident spectrum including one or more of a UV wavelength, a visible wavelength, and a near infrared wavelength and emits light having an emission spectrum including one or more of visible light radiation and near infrared radiation, where different yarn types absorb different wavelengths from the incident spectrum and/or emit an emission spectrum with different wavelengths.

Figure 5:
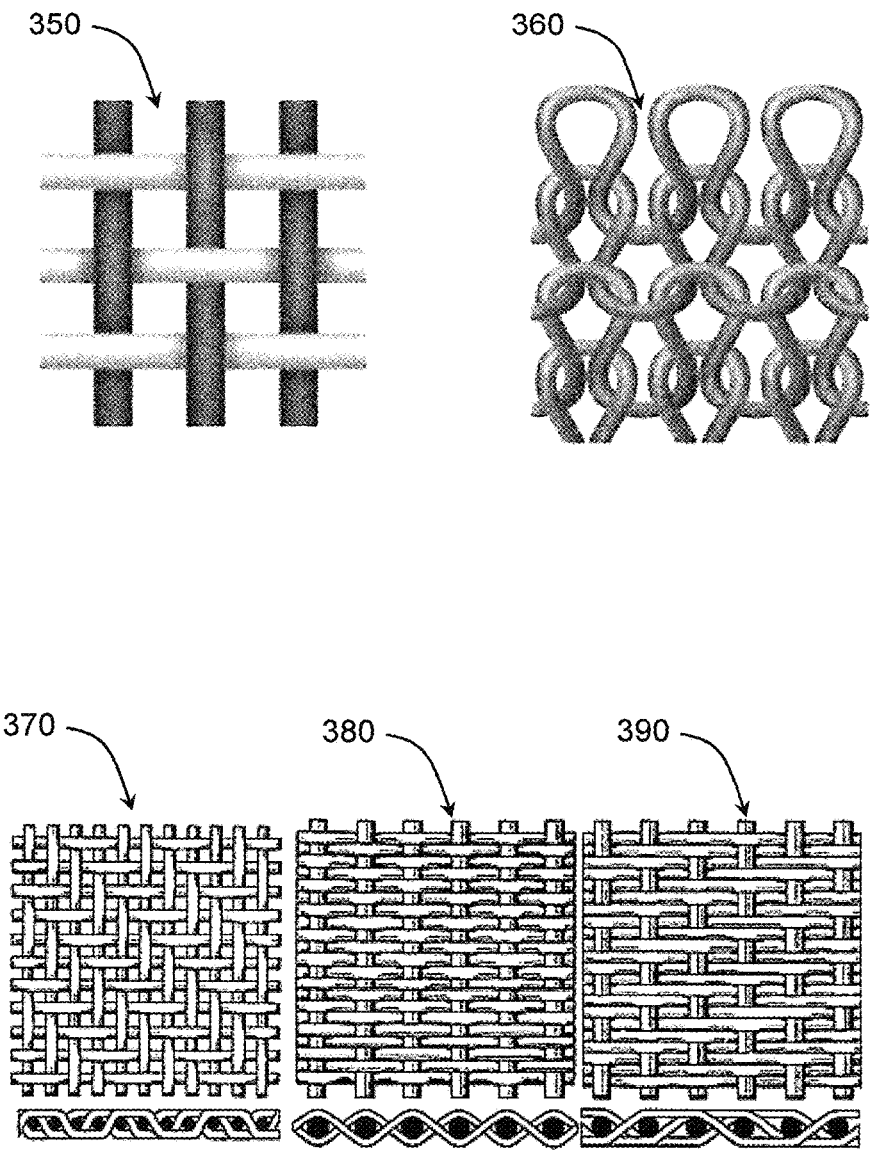
FIG. 5 illustrates examples of woven and knitted characters for the network of yarns.

The network of yarns can have any woven character, fleece and/or any knitted character. FIG. 5 illustrates an example of woven character 350, in which yarns are assembled in parallel using weaving, and an example of knitted character 360, in which yarns are knitted into a fabric. Other examples shown in FIG. 5 include twilled 370, plain dutch weave 380, and twilled dutch weave 390, but any woven, fleece, or knitted character can be utilized in the light management systems disclosed herein.

Figure 6:
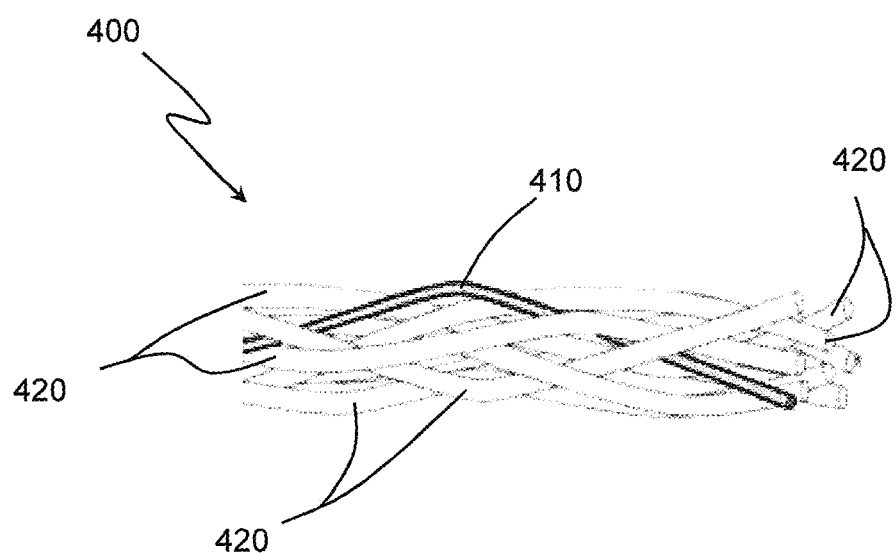
FIG. 6 is a schematic drawing of a multifilament yarn.
Figure 7:
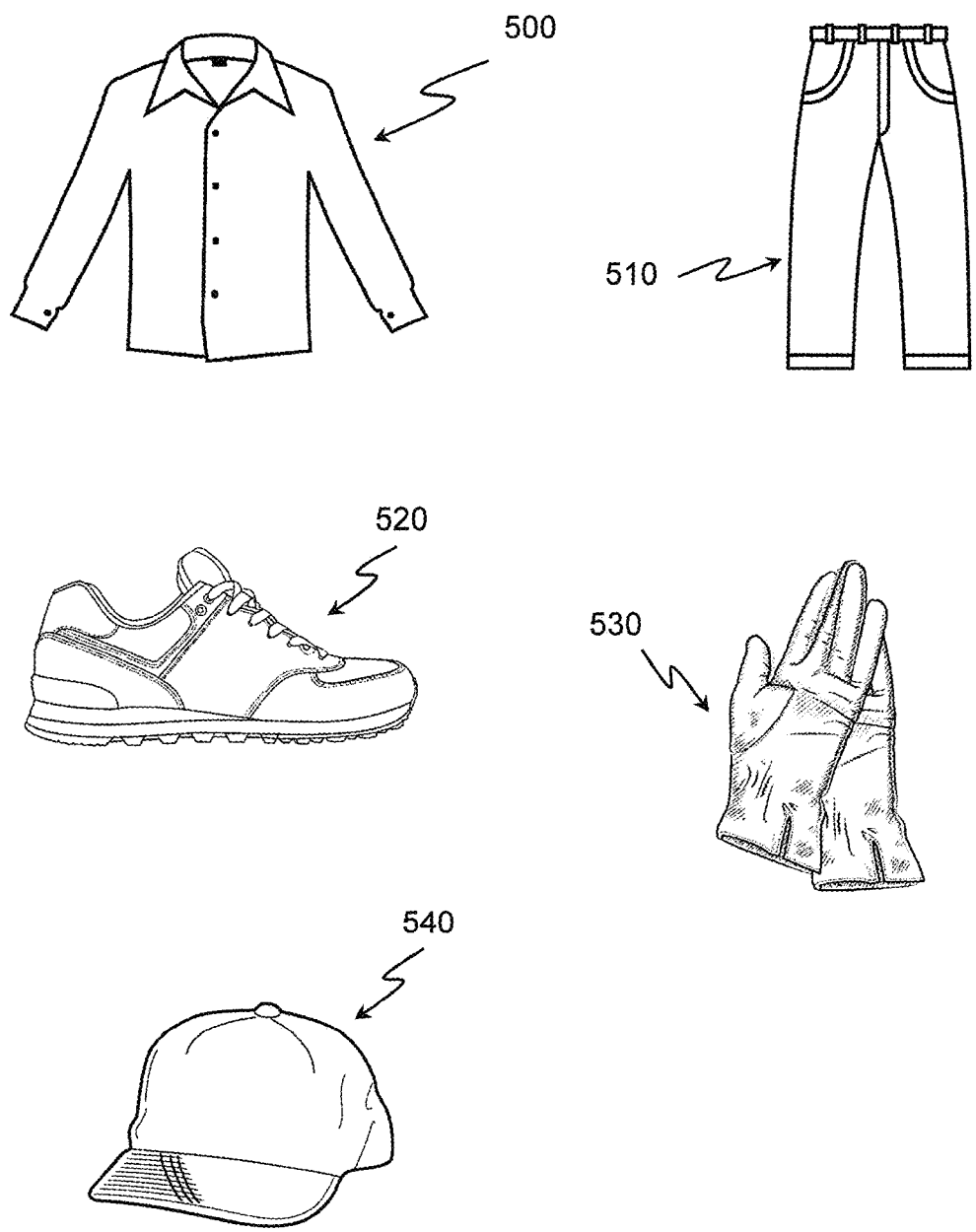

The yarns can be in any suitable form. For example, the yarns can be monofilament or multifilament, staple or continuous. FIG. 6 is a schematic drawing of a multifilament yarn 400. In exemplary embodiments, the multifilament yarn 400 includes at least one of a first filament type 410 and a plurality of a second filament type 420. The different filament types can be incorporated into the textile material in any suitable manner. The first filament type 410 absorbs an incident spectrum including one or more of a UV wavelength, a visible wavelength, and a near infrared wavelength and emits light having an emission spectrum including one or more of visible light radiation and near infrared radiation. One (or more than one) of such a first filament type 410 can be incorporated into the multifilament yarn 400. Alternatively, a majority of the filaments in the multifilament yarn 400 can be of such a first filament type 410. However, any, a subset, or all of the filaments in the multifilament yarn 400 can be of a type that absorb an incident spectrum including one or more of a UV wavelength, a visible wavelength, and a near infrared wavelength and emits light having an emission spectrum including one or more of visible light radiation and near infrared radiation. Accordingly, the multifilament yarn 400 can incorporate one or more filament types each of which absorb an incident spectrum including one or more of a UV wavelength, a visible wavelength, and a near infrared wavelength and emits light having an emission spectrum including one or more of visible light radiation and near infrared radiation, where different first filament types 420 absorb different wavelengths from the incident spectrum and/or emit an emission spectrum with different wavelengths.

In addition, the yarns can be staple or multi-filament, where staple refers to fiber of discrete length and multi-filament refers to a continuous fiber. Further, the yarns may be composite yarns with desired properties and aesthetics resulting from, for example, yarn mixes (mixed colors, mixed deniers, mixed cross-sections, mixed bicomponent/homofilament, etc.). Also for example, the yarns may be textured by, for example, forming crimps, loops, coils, or crinkles in the filaments, which affects the behavior and hand of textile materials made from them.

The yarns include a textile grade, polymeric host material 220. Suitable textile grade, polymeric host material 220 includes a homopolymer or a copolymer or a long-chain polymer selected from the group consisting of polyesters, polyamides, olefins, acrylics, poly(methyl methacrylate) (PMMA), polylactic acid (PLA), and polycarbonates.

In exemplary embodiments, the textile grade, polymeric host material has an intrinsic viscosity (IV) in a range of 0.5 to 1.0 dL/g.

The yarns also include one or more fluorescent components. Example fluorescent components include one or more of a dye and a quantum dot.

The fluorescent component is characterized by having either or both an emission spectrum including visible light radiation having a quantum efficiency of 90% and above, and an emission spectrum in the near infrared range having a quantum efficiency of 50% and above. When the fluorescent component is a dye, the dye includes one or more of a perylene dye, a cyanine dye, a rhodamine dye, a coumarine dye, a dye belonging to the class of anthrapyridone dyes, thioxanthene dyes and thioindigoid dyes, or mixtures thereof.

In general, the higher the molecular weight of the fluorescent components, the less weight percent of the fluorescent components is necessary to obtain the desired intensity of emission spectrum. Also in general, the higher the quantum efficiency of the fluorescent components, the less weight percent of the fluorescent components is necessary to obtain the desired intensity of emission spectrum. Thus, in exemplary embodiments, the amount of fluorescent components in the textile grade, polymeric host material is in the range of 0.01 weight % (wt. %) to 1 wt. %. Alternatively, the amount of fluorescent components in the textile grade, polymeric host material is in the range of 0.01 wt. % to 0.1 wt. %, or is in the range of 0.05 wt. %, 0.10 wt. %, 0.15 wt. % or 0.20 wt. % to 0.10 wt. %, 0.25 wt. %, or 0.50 wt. %. In exemplary embodiments, 0.015 wt. % of a red anthrapyridone fluorescent dye was used, a combination of 0.025 wt. % of a perylene fluorescent dye and 0.06 wt. % of a cyanine fluorescent dye (which is a near infrared dye) was used, or a combination of 0.045 wt. % of a fluorescent dye called Vat Violet 3, which belongs to the class of thioindigoid dyes, and 0.045 wt. % of a cyanine fluorescent dye (which is a near infrared dye) was use.

Because of its strong UV light absorbing capabilities that competes with UV absorption capabilities of the fluorescent components, the amount of titanium dioxide ($TiO_2$) included in the yarns is minimized. In general, as the amount of titanium dioxide increase, decreases spontaneous emission (as the absorption performance decreases). Thus, in exemplary embodiments, the amount of titanium dioxide is less than 2.0 wt. %, alternatively less than 1.0 wt. %. It is preferred that there be no titanium dioxide in the yarns, i.e., that the yarns are titanium dioxide free.

Individual yarns can be any desired cross-section. For example, individual monofilament yarn can have a circular cross-section and be, for example, on the order of 10 microns in diameter. Also for example, individual monofilament yarn can have a multilobal cross section, such as a trilobal cross section, and be, for example, on the order of 10 microns in diameter. Multifilament yarn can be of any type, including FFT (false twist textured) or AJT (air jet textured).

The yarns and fabrics or textile materials incorporating the yarns can be manufactured using suitable methods. For example, a first textile grade, polymeric host material and at least one of a first fluorescent component and a second fluorescent component can be mixed using extrusion techniques to form a masterbatch. In exemplary embodiments, the masterbatch has a concentration of the fluorescent component of 2% to 20%. The masterbatch is then mixed with a volume of a second textile grade, polymeric host material to produce a feedstock in which a total amount of fluorescent component in the feedstock is 0.01 wt. % to 1 wt. %, alternatively in the range of 0.05 wt. %, 0.10 wt. %, 0.15 wt. % or 0.20 wt. % to 0.10 wt. %, 0.25 wt. %, or 0.50 wt. %.

The feedstock is then processed into flat yarn. An example technique for processing the feedstock into flat yarn is melt spinning. But other techniques can be used, such as wet spinning or dry spinning. The flat yarn can be further processed by texturing to form a textured yarn or by cutting to form a staple yarn. Texturing the yarn helps to ensure light is emitted from the side surface along the length of the yarns (as described earlier with reference to FIG. 3B). As discloses elsewhere herein, when exposed to visible light, the textured yarn or staple yarn emits radiation having an emission spectrum including at least one peak in a range of 600 nm to 1200 nm. Texturing also serves secondary purposes including creating a softer and better touch ("hand feel") and improving moisture control.

Suitable textile grade, polymeric host materials and fluorescent components can be any such materials and components disclosed elsewhere herein. In exemplary embodiments, the textile grade, polymeric host material has an intrinsic viscosity (IV) in a range of 0.5 to 1.0 dL/g. In some exemplary embodiments, the first textile grade, polymeric host material and the second textile grade, polymeric host material are the same, i.e., compositionally identical. In other exemplary embodiments, the first textile grade, polymeric host material and the second textile grade, polymeric host material are of a same type of polymer, e.g., are both polyesters, polyamides, olefins, acrylics, PMMA, PLA, or polycarbonates. When the first textile grade, polymeric host material and the second textile grade, polymeric host material are not the same, i.e., not compositionally identical, it is preferable that the first textile grade, polymeric host material has a higher intrinsic viscosity (IV) than the second textile grade, polymeric host material.

In exemplary embodiments, the fluorescent components include one or more of a dye and a quantum dot and, when the fluorescent component is a dye, the dye includes one or more of a perylene dye, a cyanine dye, a rhodamine dye, a coumarine dye, a dye belonging to the class of anthrapyridone dyes, thioxanthene dyes and thioindigoid dyes, or mixtures thereof. In some exemplary embodiments, the first fluorescent component has a quantum efficiency of more than 90% for emission at visible wavelengths and the second fluorescent component has a quantum efficiency of more than 50% for emission at near infrared wavelengths.

It should be noted that prior to mixing, the optically clear, polymeric host material can be processed using conventional pretreatment, drying and crystallization techniques. Also, the manufactured textured yarn or staple yarn can be further manufactured into fabrics or textile materials or an article of apparel using suitable methods known in the textile industry.

Light management systems disclosed herein can be used to have a strong spontaneous emission that releases most of its absorbed energy from sunlight in the form of light of visible wavelengths and/or near infrared wavelengths.

Light management systems disclosed herein can be used to have a high absorption at the UV wavelengths.

Light management systems disclosed herein can be used to have a strong emission of visible wavelengths and/or near infrared wavelengths.

The light management system can be embodied in any suitable article of apparel. Such apparel can be made with yarns that are embedded with fluorescent components (dyes and/or quantum dots). The fluorescent components can spontaneously emit light at visible or near-Infrared wavelengths.

Several example articles of apparel are illustrated in FIGS. 7 to 10. For example, the article of apparel can be clothing, such as a shirt 500, a pant 510, a short, a sock. Other suitable articles of clothing include a footwear 520, a hand covering, such as glove 530, a wrist band, a head band, and a head covering, which includes, for example, a hat 540, a scarf, or a helmet. In addition, suitable articles of clothing include athletic gear such as work out clothing 600 and uniforms. Further, the light management system can be embodied in all or a portion of any suitable article of apparel, such as an arm sleeve, a calf sleeve, an arm band 610, or bandage material. The light management system can also be embodied in all or a portion of any suitable article of apparel 620 used for other mammals, such as dogs, cats or horses.

In addition to all or a portion of articles of apparel, the light management system can be incorporated into bedding or a towel or a sunshade structure, such as a beach umbrella, a patio umbrella, or an awning.

When a plurality of yarns is incorporated into a textile material, the emission from the side surface at substantially multiple points throughout the yarn, i.e., light is absorbed and emitted locally at discreet points (see, e.g., FIG. 3B) results in area of the textile material emitting the emission spectrum. This area can be the entire article of apparel or can be a plurality of discreet areas within the article of apparel. In some embodiments, the plurality of discreet areas can be located within the article of apparel to correspond to discreet body parts. For example, where the article of apparel is a shirt, the plurality of discreet areas can be located within the shirt to correspond to the discreet body parts of any one or more of a shoulder, an elbow, a bicep, a tricep, etc. In another example, where the article of apparel is a pant or a short, the plurality of discreet areas can be located within the pant or a short to correspond to the discreet body parts of any one or more of a knee, a hip, a quadriceps, a hamstring, etc. In still another example, where the article of apparel is a headgear, the plurality of discreet areas can be located within the headgear to correspond to the discreet body parts of any one or more of a forehead, a crown, a temple, etc.

Although described herein in connection with an article of apparel, such as clothing, footwear, head covering, and athletic gear, it should be understood that the structure and methods and principles disclosed herein can be similarly applied to other textile-based objects, such as bedding and towels, and sun shade structures. In each instance, the textile-based objects can absorb an incident spectrum and, can spontaneously emit light.

The textile materials may be implemented in conjunction with other existing special performance textile technologies, like geotextiles, nanotechnology textiles, push/pull fabric constructions, phase change material (PCM) textiles, temperature/humidity gradient textiles, etc., designed for applications like moisture management, waterproofing, comfort cooling, and comfort heating. Functional finishes and coatings for antimicrobial, antistatic, crease-resistance, flame-resistance, water and oil repellency, waterproofing, etc. are all also compatible with the textile materials and can provide additional properties without affecting the performance of the textile materials, as well as articles of apparel comprising such textile materials, themselves.

Figures 14A, 14B:
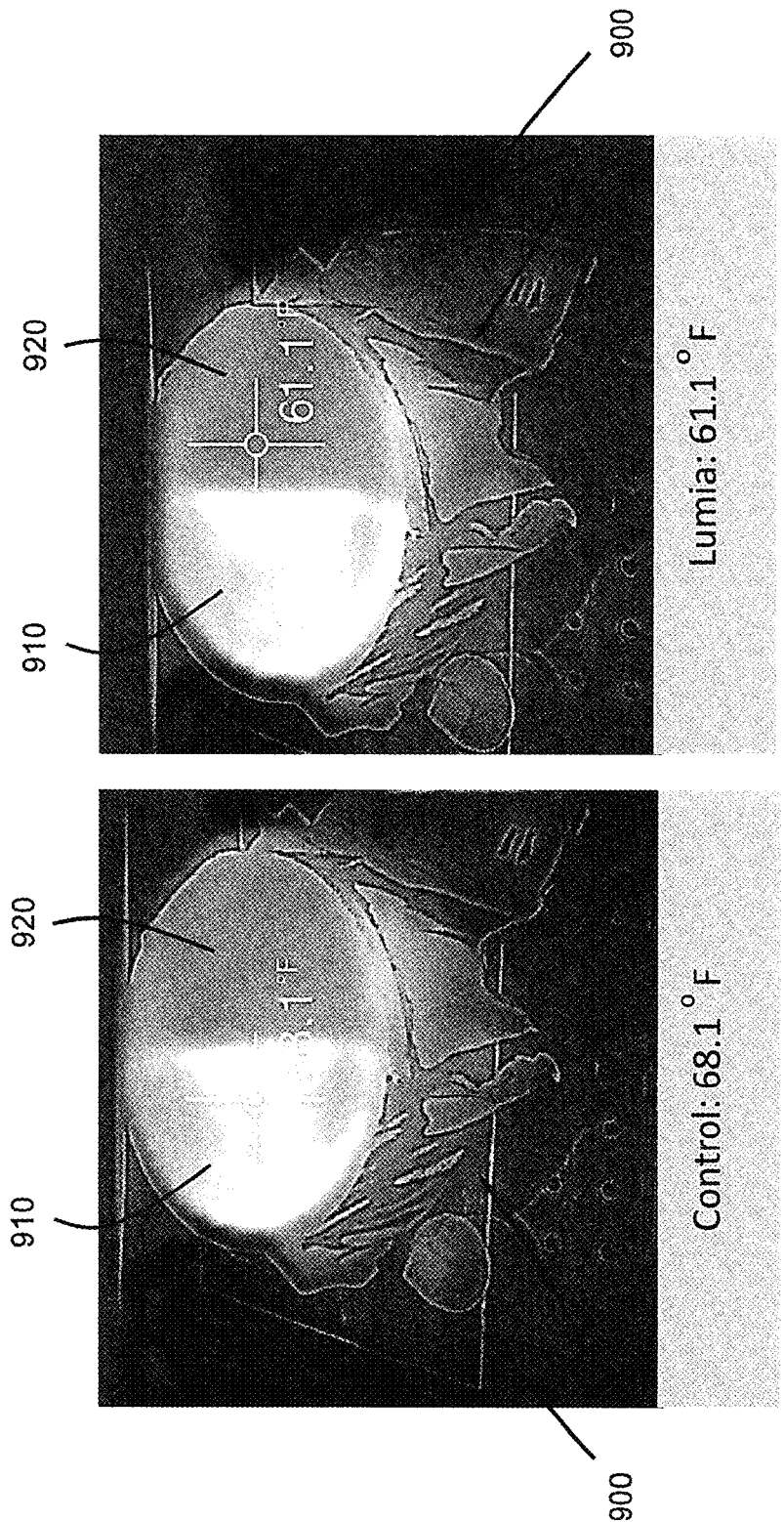
FIGS. 14A and 14B show experimental results showing the temperature difference between an inventive sample and a comparative example.

A property of the articles of apparel is a "shading" effect whereby the yarns/fabric do not heat up under the sun as much as would conventionally be expected because the use of fluorescent components with high quantum efficiency results in yarns that release most of the absorbed energy via the production of red and/or near infrared emitted light and is not retained as heat-producing energy (see FIGS. 14A and 14B and related disclosure).

Another property of the articles of apparel is extra protection against short wavelengths having damaging effect on the human skin, which occurs by converting the energy in the potentially damaging, short wavelengths into energy at red and/or near-infrared emitted light wavelengths. In some embodiments, the textile material and apparel incorporating the textile material has a UPF (ultraviolet protection factor) of at least 50. The UPF is a numerical rating given to clothing to indicate how effectively the fabric blocks ultraviolet (UV) radiation. A UPF rating of 50 means that only 1/50th (or 2%) of the UV radiation can penetrate the textile material.

One more property of the articles of apparel is the "shielding" effect that provides extra protection from being visible. The strong emission at the visible wavelengths creates a light-filling effect that shields the object behind the apparel even when the knit and/or weave structure would be, otherwise, shear.

An additional property of the articles of apparel is the "warming" effect under the sunlight in cold weather conditions. The strong emission at the visible and/or near-infrared wavelength when reaching the back of the first layer of apparel can be absorbed by the secondary layer to produce heat. The first layer can insulate the secondary layer from the outside cold weather.

A secondary property of the articles of apparel is the "functional covering" effect. The strong emission at the visible and/or near-infrared wavelength when reaching the backside of the apparel can interact with a photovoltaic device, which absorbs at least a portion of the emission spectrum to cause a flow of electrons in the photovoltaic device.

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

EXAMPLE 1

A fabric was constructed using yarns made from textile-grade polyester (PET) with IV=0.65 dL/g. The PET is "super bright," i.e., it contains 0.00% titanium dioxide. The yarn includes 0.015 wt. % of a red anthrapyridone fluorescent dye called "solvent red dye 149" that is distributed homogenously in the PET polymeric host material. The fabric was stretched taut and, in separate experiments, exposed to a first spectrum (700 in FIG. 11A) containing blue light with a peak (705 in FIG. 11A) at 450 nm and exposed to a second spectrum (710 in FIG. 11B) containing green light with a peak (715 in FIG. 11B) at 525 nm.

Figure 11A:
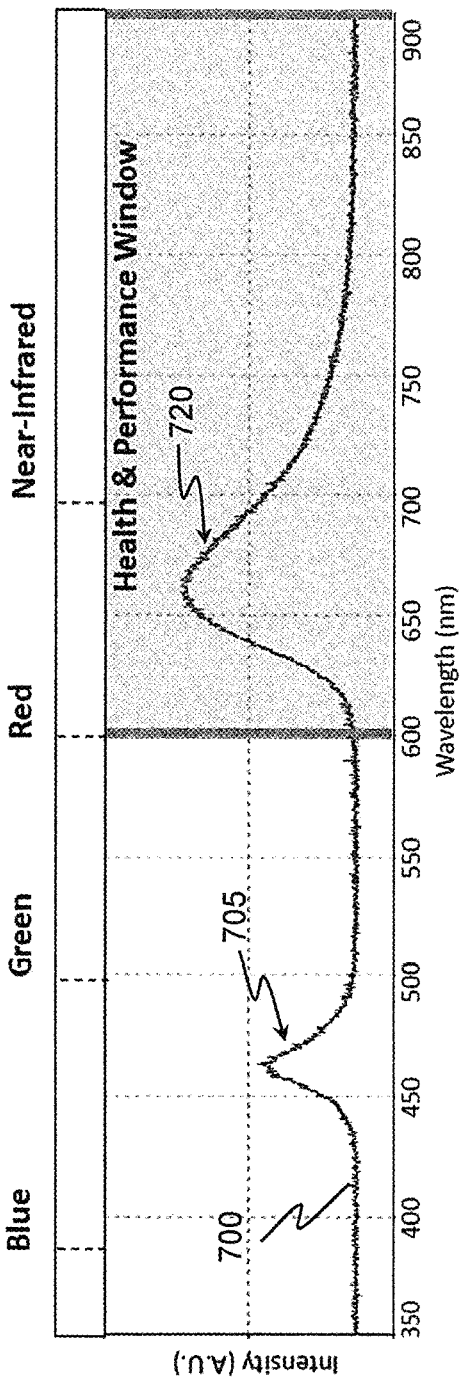
FIGS. 11A to 11B are experimental results showing spectra of a fabric excited by blue light and green light.
Figure 11B:
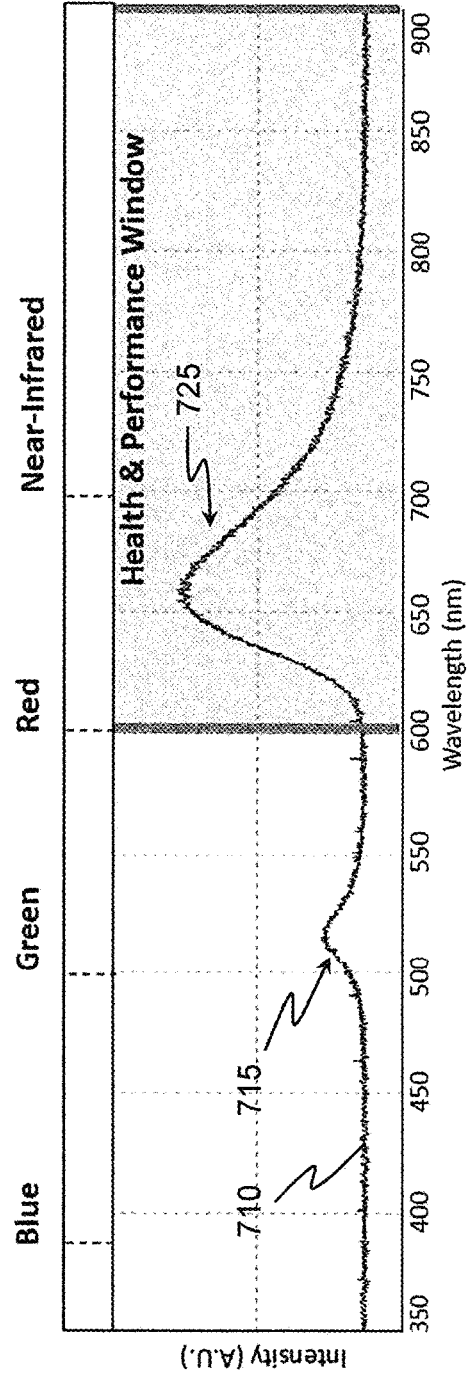

FIG. 11A shows that the fabric exposed to the first spectrum 700 emits a spectrum of red light with a peak (725 in FIG. 11A) at 670 nm and a full width at half maximum (FWHM) of about 85 nm. FIG. 11B shows that the fabric exposed to the second spectrum 710 also emits a spectrum of red light with a peak (725 in FIG. 11B) at 670 nm and a full width at half maximum (FWHM) of about 82.5 nm.

From FIGS. 11A and 11B, one can observe the following. First, the peak wavelength in the emitted spectrum is independent of the incident spectrum 700,710 (as both a peak at 450 nm and a peak at 525 nm in the incident spectra 700,710 resulted in an emission spectrum with a peak at 670 nm). Second, although the first spectrum 700 containing incident blue light with a peak at 450 nm was approximately double the magnitude of the second spectrum 710 containing incident green light with a peak at 525 nm, the emission peak at 670 nm for the emitted spectrum in each experiment had approximately the same magnitude.

EXAMPLE 2

A fabric was constructed using yarns made from textile-grade polyester (PET) with IV=0.65 dL/g. The PET is "super bright," i.e., it contains 0.00% titanium dioxide. The yarn includes 0.025 wt. % of a perylene fluorescent dye and 0.06 wt. % of a cyanine fluorescent dye (which is a near infrared dye), both of which are distributed homogenously in the PET polymeric host material. The fabric was stretched taut and, in separate experiments, exposed to a first spectrum (750 in FIG. 12A) containing blue light with a peak (755 in FIG. 12A) at 390 nm, exposed to a second spectrum (760 in FIG. 12B) containing green light with a peak (765 in FIG. 12B) at 525 nm, and exposed to a third spectrum (770 in FIG. 12C) containing red light with a peak (775 in FIG. 12C) at 630 nm.

Figure 12A:
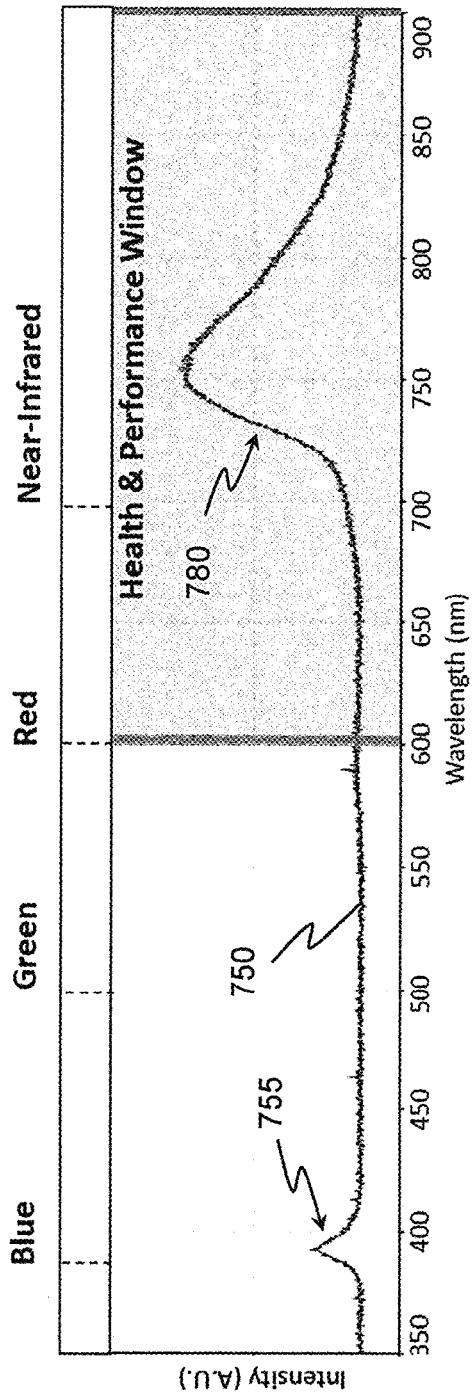
FIGS. 12A to 12C are experimental results showing spectra of a fabric excited by blue, green and red light.
Figure 12B:
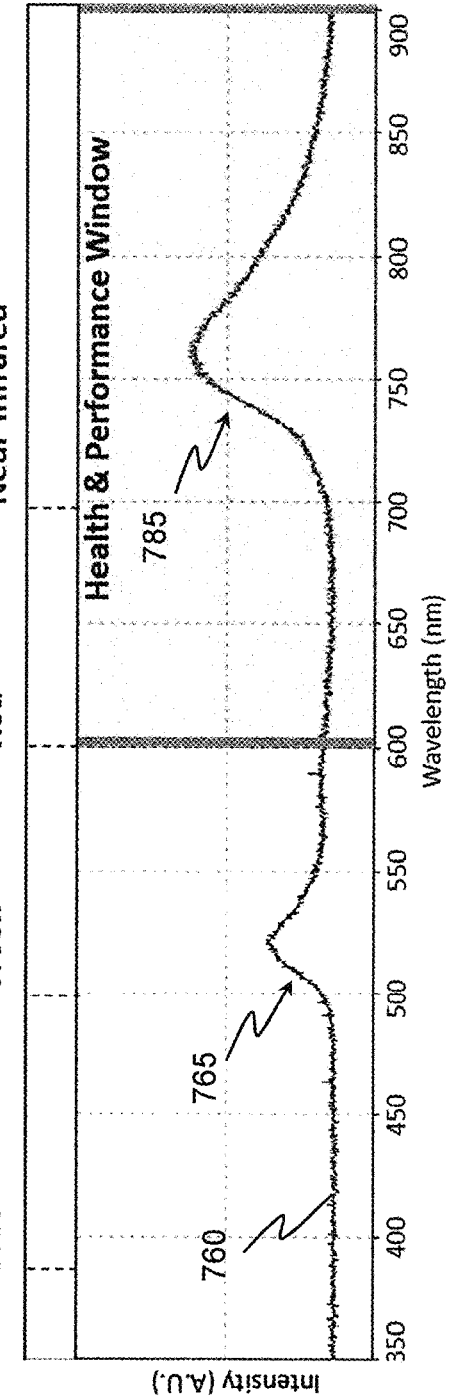
Figure 12C:
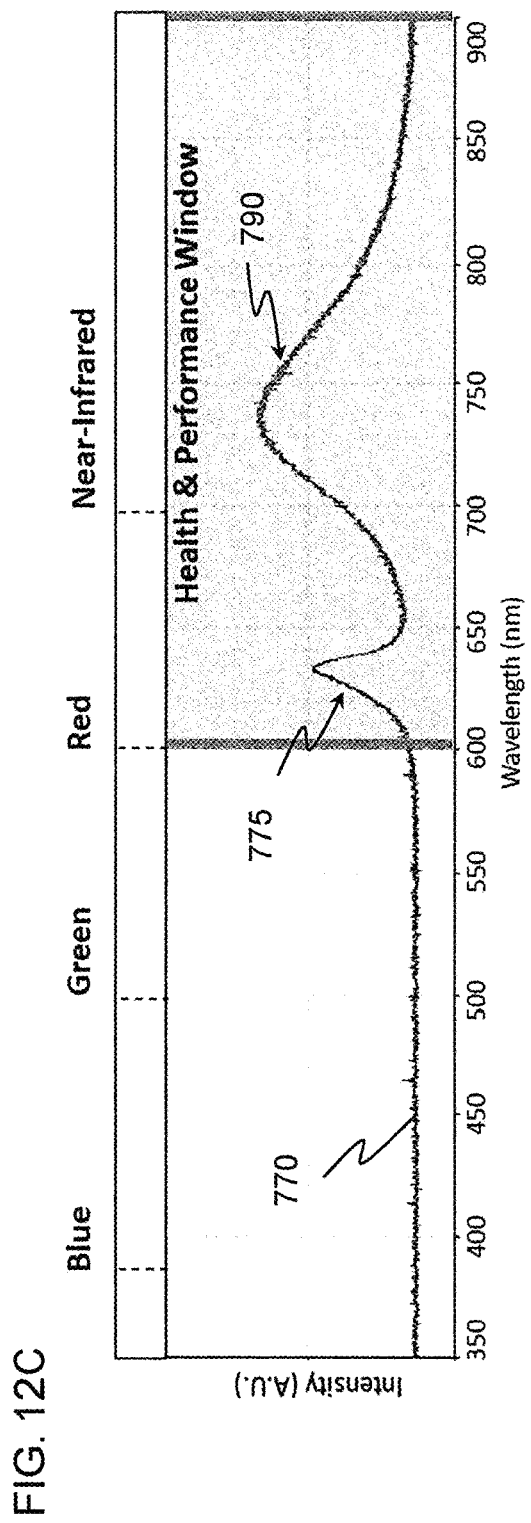

FIG. 12A shows that the fabric exposed to the first spectrum 750 emits a spectrum of near infrared (NIR) light with a peak (780 in FIG. 12A) at 756 nm and a full width at half maximum (FWHM) of about 85 nm. FIG. 12B shows that the fabric exposed to the second spectrum 760 also emits a spectrum of NIR light with a peak (785 in FIG. 12B) at 756 nm and a full width at half maximum (FWHM) of about 86 nm. FIG. 12C shows that the fabric exposed to the third spectrum 770 also emits a spectrum of NIR light with a peak (790 in FIG. 12C) at 745 nm and a full width at half maximum (FWHM) of about 103 nm. In each instance, the peak of 750±6 nm for the emitted light is a therapeutic wavelength within the health and performance window.

EXAMPLE 3

A fabric was constructed using yarns made from textile—grade polyester (PET) with IV=0.65 dL/g. The PET is "super bright," i.e., it contains 0.00% titanium dioxide. The yarn includes 0.045 wt. % of a fluorescent dye called Vat Violet 3, which belongs to the class of thioindigoid dyes, and 0.045 wt. % of a cyanine fluorescent dye (which is a near infrared dye), both of which are distributed homogenously in the PET polymeric host material. The fabric was stretched taut and, in separate experiments, exposed to a first spectrum (800 in FIG. 13A) containing blue light with a peak (805 in FIG. 13A) at 400 nm, and exposed to a second spectrum (810 in FIG. 13B) containing green light with a peak (815 in FIG. 13B) at 525 nm.

Figure 13A:
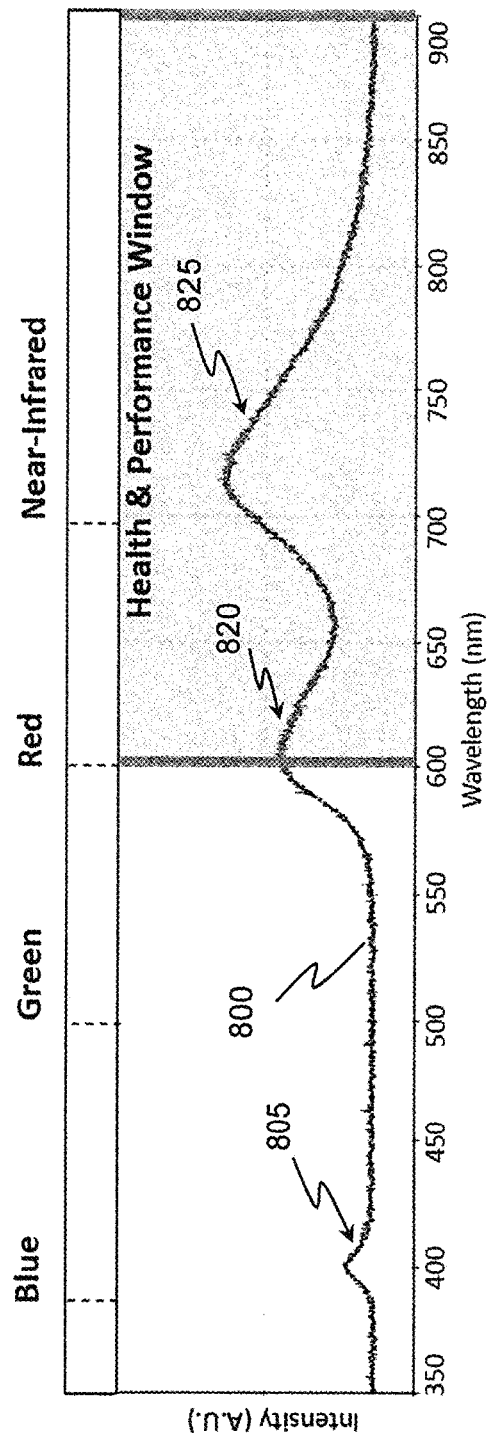
FIGS. 13A to 13B are experimental results showing spectra of a fabric excited by blue light and green light.

FIG. 13A shows that the fabric exposed to the first spectrum 800 emits a spectrum with two peaks—a first peak (820 in FIG. 13A) at 600 nm and a full width at half maximum (FWHM) of about 75 nm and a second peak (825 in FIG. 13A) at 730 nm and a full width at half maximum (FWHM) of about 113 nm. The first peak 820 is a red emission peak and the second peak 825 is a NIR emission peak.

Figure 13B:
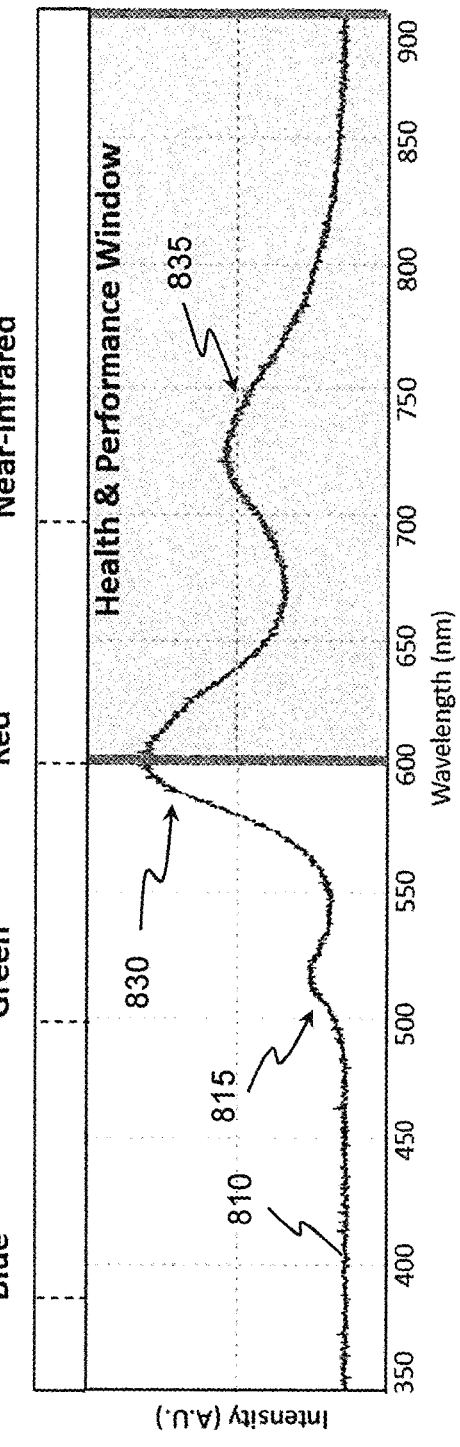

FIG. 13B shows that the fabric exposed to the second spectrum 810 emits a spectrum of with two peaks—a first peak (830 in FIG. 13B) at 600 nm and a full width at half maximum (FWHM) of about 75 nm and a second peak (835 in FIG. 13B) at 730 nm and a full width at half maximum (FWHM) of about 125 nm. The first peak 830 is a red emission peak and the second peak 835 is a NIR emission peak.

The spectra shown in FIGS. 11A-B, 12A-C, and 13A-B are presented graphically as arbitrary units of intensity versus wavelength in nm and, in each graph, intensity (arbitrary units) on the y-axis ranges from zero to 10000 arbitrary units and wavelength on the x-axis ranges from 350 nm to 900 nm.

FIGS. 14A and 14B show experimental results for a textile material consistent with that disclosed herein and demonstrating that the inventive textile material is cooler under imitated sunlight conditions than that of a comparative example textile material. The experimental details include: the portion 910 of the fabric sample 900 made from the comparative example textile material (see FIG. 14A) is 2/70/68 (plys/denier/filaments) continuous multifilament polyester yarn which has been exhaust dyed to form a pink fabric; the portion 920 of the fabric sample 900 made from the inventive textile material (see FIG. 14B) is 2/70/68 continuous multifilament polyester yarn solution dyed with a perylene dye to form a pink fabric; illumination source was a solar simulator operated in continuous mode at a power level of 1 sun (equivalent to 100 mW/cm$^2$) at a distance of 4 inches above the surface of sample 900 and oriented at 90 degrees to the surface of the sample. The sample, and thus each of the comparative example textile material portion 910 and the inventive textile material portion 920, were illuminated by the illumination source and allowed to reach a steady state temperature condition (e.g., after about 3 minutes) before the temperature was measured. The images in FIGS. 14A and 14B were taken by a FLIR infrared thermal camera. The location in each figure at which the temperature was measured is indicated by a cross-hair. As shown in FIG. 14A, the temperature reading of the comparative example textile material portion 910 at steady state temperature conditions was 68.1° F. As shown in FIG. 14B, under the same testing conditions as the comparative example, the inventive textile material portion 920 had a temperature of 61.1° F. at steady state temperature conditions. Thus, the inventive textile material portion 920 was 7° F. cooler than the comparative example textile material portion 910. The images in FIGS. 14A and 14B demonstrate that a textile material incorporating yarns that include a textile grade, polymeric host material with 0.01 wt. % to 1.0 wt. % of one or more fluorescent components as disclosed herein provides a UV blocking effect, which can be perceived by someone wearing apparel incorporating such yarns as a cooling effect.

In another aspect, human sweat is virtually odorless to humans. However, the rapid multiplication of bacteria living on our skin that occurs in the presence of sweat and the bacterial break down of sweat into acids that leads to an odor or unpleasant smell. The wavelengths of light disclosed herein and emitted by the light management apparel have been shown to have an anti-bacterial effect. These wavelengths include blue, green, red and near-infrared. Thus, in another effect of the light management apparel disclosed herein, the light management apparel disclosed herein directs emitted light toward the body and reduces the bacterial population, both on the skin as well as in the apparel itself. This results in a reduction in odor or unpleasant smell.

While reference has been made to specific embodiments, it is apparent that other embodiments and variations can be devised by others skilled in the art without departing from their spirit and scope. The appended claims are intended to be construed to include all such embodiments and equivalent variations.

What is claimed is:

1. A method of protection from solar radiation, the method comprising:
    interposing an article of apparel between a source of solar radiation and a mammalian skin,
    wherein the article of apparel absorbs an incident spectrum including one or more of a UV wavelength, a visible wavelength, and a near infrared wavelength and emits light having an emission spectrum including one or more of visible light radiation and near infrared radiation,
    wherein the light having an emission spectrum including one or more of visible light radiation and near infrared radiation is emitted from the article of apparel in a direction toward a wearer of the article of apparel, and
    wherein the emission spectrum includes one or both of the following:
        (a) one or more of a peak between 700 nm and 800 nm with a full width at half maximum (FWHM) of 100 nm to 150 nm and a peak between 800 nm and 900 nm with a full width at half maximum (FWHM) of 100 nm to 150 nm, and
        (b) one or more of a peak between 590 nm and 700 nm with a full width at half maximum (FWHM) of 50 nm to 100 nm and a peak between 700 nm and 900 nm with a full width at half maximum (FWHM) of 50 nm to 150 nm.

2. The method according to claim 1, wherein the method provides a level of skin protection of at least UPF 50.

3. The method according to claim 1, wherein the article of apparel is electrically passive.

4. The method according to claim 1, wherein the article of apparel, comprises:
    a textile material including a network of yarns, wherein the yarns include one or more of a textured yarn and a staple yarn;
    wherein each yarn in the network of yarns includes a textile grade, polymeric host material and 0.01 wt. % to 1.0 wt. % of one or more fluorescent components,
    wherein the fluorescent component having an emission spectrum including visible light radiation has a quantum efficiency of 90% and above, and
    wherein the fluorescent component having an emission spectrum in the near infrared range has a quantum efficiency of 50% and above.

5. The method according to claim 4, wherein the fluorescent component includes one or more of a dye and a quantum dot.

6. The method according to claim 5, wherein the dye includes one or more of a perylene dye, a cyanine dye, a rhodamine dye, a coumarine dye, and a dye belonging to the class of anthrapyridone dyes, thioxanthene dyes and thioindigoid dyes.

7. The method according to claim 6, wherein the dye includes one or more species of fluorescent dyes.

8. The method according to claim 4, wherein the textile grade, polymeric host material is a homopolymer or a copolymer or a long-chain polymer and is selected from the group consisting of polyesters, polyamides, olefins, acrylics, PMMA, PLA, and polycarbonates, and wherein the textile grade, polymeric host material has an intrinsic viscosity (IV) in a range of 0.5 to 1.0 dL/g.

9. The light management system according to claim 8, wherein each yarn in the network of yarns further includes less than 2.0 wt. % titanium dioxide.

10. The method according to claim 4, wherein the light having an emission spectrum including one or more of visible light radiation and near infrared radiation emitted from the article of apparel is emitted from a plurality of locations along a length of one or more of the yarns.

11. A method of shading, the method comprising:
interposing a textile material between a source of solar radiation and a mammalian skin,
wherein the textile material absorbs an incident spectrum including one or more of a UV wavelength, a visible wavelength, and a near infrared wavelength and emits light having an emission spectrum including one or more of visible light radiation and near infrared radiation,
wherein the light having an emission spectrum including one or more of visible light radiation and near infrared radiation is emitted from the textile material in a direction toward the mammalian skin, and
wherein the emission spectrum includes one or both of the following:
(a) one or more of a peak between 700 nm and 800 nm with a full width at half maximum (FWHM) of 100 nm to 150 nm and a peak between 800 nm and 900 nm with a full width at half maximum (FWHM) of 100 nm to 150 nm, and
(b) one or more of a peak between 590 nm and 700 nm with a full width at half maximum (FWHM) of 50 nm to 100 nm and a peak between 700 nm and 900 nm with a full width at half maximum (FWHM) of 50 nm to 150 nm.

12. The method according to claim 11, wherein a temperature of the shaded mammalian skin is reduced by at least 3 degrees Fahrenheit as compared to mammalian skin without the interposed article of apparel.

13. The method according to claim 11, wherein the article of apparel is electrically passive.

14. The method according to claim 11, wherein the textile material includes a network of yarns,
wherein the yarns include one or more of a textured yarn and a staple yarn,
wherein each yarn in the network of yarns includes a textile grade, polymeric host material and 0.01 wt. % to 1.0 wt. % of one or more fluorescent components,
wherein the fluorescent component having an emission spectrum including visible light radiation has a quantum efficiency of 90% and above, and
wherein the fluorescent component having an emission spectrum in the near infrared range has a quantum efficiency of 50% and above.

15. The method according to claim 14, wherein the fluorescent component includes one or more of a dye and a quantum dot.

16. The method according to claim 15, wherein the dye includes one or more of a perylene dye, a cyanine dye, a rhodamine dye, a coumarine dye, and a dye belonging to the class of anthrapyridone dyes, thioxanthene dyes and thioindigoid dyes.

17. The method according to claim 16, wherein the dye includes one or more species of fluorescent dyes.

18. The method according to claim 14, wherein the textile grade, polymeric host material is a homopolymer or a copolymer or a long-chain polymer and is selected from the group consisting of polyesters, polyamides, olefins, acrylics, PMMA, PLA, and polycarbonates, and wherein the textile grade, polymeric host material has an intrinsic viscosity (IV) in a range of 0.5 to 1.0 dL/g.

19. The light management system according to claim 18, wherein each yarn in the network of yarns further includes less than 2.0 wt. % titanium dioxide.

20. The method according to claim 14, wherein the light having an emission spectrum including one or more of visible light radiation and near infrared radiation emitted from the article of apparel is emitted from a plurality of locations along a length of one or more of the yarns.

21. A method of shading an object from solar radiation, the method comprising:
interposing a textile material between a source of solar radiation and the object,
wherein the textile material absorbs an incident spectrum including one or more of a UV wavelength, a visible wavelength, and a near infrared wavelength and emits light having an emission spectrum including one or more of visible light radiation and near infrared radiation,
wherein the light having an emission spectrum including one or more of visible light radiation and near infrared radiation is emitted from the textile material in a direction toward the object, and
wherein the emission spectrum includes one or both of the following:
(a) one or more of a peak between 700 nm and 800 nm with a full width at half maximum (FWHM) of 100 nm to 150 nm and a peak between 800 nm and 900 nm with a full width at half maximum (FWHM) of 100 nm to 150 nm, and
(b) one or more of a peak between 590 nm and 700 nm with a full width at half maximum (FWHM) of 50 nm to 100 nm and a peak between 700 nm and 900 nm with a full width at half maximum (FWHM) of 50 nm to 150 nm.

22. The method according to claim 21, wherein a temperature of the shaded object is reduced by at least 3 degrees Fahrenheit as compared to the object without the interposed article of apparel.

23. The method according to claim 21, wherein the textile material is electrically passive.

24. The method according to claim 21, wherein the textile material includes a network of yarns,
wherein the yarns include one or more of a textured yarn and a staple yarn,
wherein each yarn in the network of yarns includes a textile grade, polymeric host material and 0.01 wt. % to 1.0 wt. % of one or more fluorescent components, wherein the fluorescent component having an emission spectrum including visible light radiation has a quantum efficiency of 90% and above, and wherein the fluorescent component having an emission spectrum in the near infrared range has a quantum efficiency of 50% and above.

25. The method according to claim 24, wherein the fluorescent component includes one or more of a dye and a quantum dot.

26. The method according to claim 25, wherein the dye includes one or more of a perylene dye, a cyanine dye, a rhodamine dye, a coumarine dye, and a dye belonging to the class of anthrapyridone dyes, thioxanthene dyes and thioindigoid dyes.

27. The method according to claim 26, wherein the dye includes one or more species of fluorescent dyes.

28. The method according to claim 24, wherein the textile grade, polymeric host material is a homopolymer or a copolymer or a long-chain polymer and is selected from the group consisting of polyesters, polyamides, olefins, acrylics, PMMA, PLA, and polycarbonates, and wherein the textile grade, polymeric host material has an intrinsic viscosity (IV) in a range of 0.5 to 1.0 dL/g.

29. The light management system according to claim 28, wherein each yarn in the network of yarns further includes less than 2.0 wt. % titanium dioxide.

30. The method according to claim 24, wherein the light having an emission spectrum including one or more of visible light radiation and near infrared radiation emitted from the textile material is emitted from a plurality of locations along a length of one or more of the yarns.

31. A light management system, comprising:
a textile material that absorbs an incident spectrum including one or more of a UV wavelength, a visible wavelength, and a near infrared wavelength and emits light having an emission spectrum including one or more of visible light radiation and near infrared radiation,
wherein the textile material is electrically passive,
wherein the light having an emission spectrum including one or more of visible light radiation and near infrared radiation is emitted from the textile material, and
wherein the emission spectrum includes one or both of the following:
(a) one or more of a peak between 700 nm and 800 nm with a full width at half maximum (FWHM) of 100 nm to 150 nm and a peak between 800 nm and 900 nm with a full width at half maximum (FWHM) of 100 nm to 150 nm, and
(b) one or more of a peak between 590 nm and 700 nm with a full width at half maximum (FWHM) of 50 nm to 100 nm and a peak between 700 nm and 900 nm with a full width at half maximum (FWHM) of 50 nm to 150 nm.

32. The light management system according to claim 31, wherein the textile material includes a network of yarns,
wherein the yarns include one or more of a textured yarn and a staple yarn;
wherein each yarn in the network of yarns includes a textile grade, polymeric host material and 0.01 wt. % to 1.0 wt. % of one or more fluorescent components,
wherein the fluorescent component having an emission spectrum including visible light radiation has a quantum efficiency of 90% and above, and
wherein the fluorescent component having an emission spectrum in the near infrared range has a quantum efficiency of 50% and above.

33. The light management system according to claim 32, wherein, interposed between a source of solar radiation and human skin, the textile material provides a level of skin protection of at least UPF 50.

34. The light management system according to claim 32, wherein, when interposed between a source of solar radiation and an object, the textile material provides at least one of a cooling effect and a shading effect.

35. The light management system according to claim 32, wherein the textile material is a first layer interposed between a source of solar radiation and human skin,
wherein at least a portion of the emission spectrum of the textile material is directed to a second layer interposed between the source of solar radiation and the human skin, the second layer closer to the human skin than the first layer, and
wherein absorption of the portion of the emission spectrum by the second layer warms the human skin.

36. The light management system according to claim 32, wherein the textile material is interposed between a source of solar radiation and a photovoltaic device,
wherein at least a portion of the emission spectrum of the textile material is directed to toward the photovoltaic device, and
wherein absorption of the portion of the emission spectrum by the photovoltaic device causes a flow of electrons in the photovoltaic device.

37. The light management system according to claim 32, wherein the textile material is interposed between a source of solar radiation and human skin,
wherein at least a portion of the emission spectrum of the textile material is directed toward the human skin and reduces a population of odor-causing bacteria.

38. The light management system according to claim 37, wherein the reduced population of odor-causing bacteria is associated with the human skin.

39. The light management system according to claim 37, wherein the reduced population of odor-causing bacteria is associated with the textile material.

* * * * *